(12) United States Patent
Hirai et al.

(10) Patent No.: US 7,380,476 B2
(45) Date of Patent: Jun. 3, 2008

(54) GAS SAMPLING BAG

(75) Inventors: Hitoshi Hirai, Kyoto (JP); Hideki Ohashi, Kyoto (JP); Toshio Mizutaka, Kyoto (JP); Kimikazu Yoda, Susono (JP); Kenichi Uchida, Susono (JP); Hiroaki Katumata, Susono (JP)

(73) Assignee: Horiba, Ltd., Minami-Ku, Kyoto (JP)

( * ) Notice: Subject to any disclaimer, the term of this patent is extended or adjusted under 35 U.S.C. 154(b) by 85 days.

(21) Appl. No.: 10/913,668

(22) Filed: Aug. 6, 2004

(65) Prior Publication Data
US 2005/0056103 A1   Mar. 17, 2005

(30) Foreign Application Priority Data
Aug. 6, 2003   (JP)   ............... 2003-287385

(51) Int. Cl.
*G01N 1/12* (2006.01)
(52) U.S. Cl. .................................... 73/864.62
(58) Field of Classification Search .... 73/23.31–23.33, 73/863.03, 864.34, 864.51, 864.62, 864.63, 73/864.73
See application file for complete search history.

(56) References Cited

U.S. PATENT DOCUMENTS 5,074,155 A    12/1991  Vecere
5,178,021 A     1/1993  Kosuth
5,239,877 A *   8/1993  Suddath et al. .......... 73/864.62
6,497,156 B2   12/2002  Dageforde

FOREIGN PATENT DOCUMENTS

| JP | 2000338015 A | 12/2000 |
| WO | WO 97/31265 | 8/1997 |
| WO | WO 02/27295 A2 | 4/2002 |

* cited by examiner

*Primary Examiner*—Robert R Raevis
(74) *Attorney, Agent, or Firm*—Brooks Kushman P.C.

(57) ABSTRACT

A gas sampling bag is capable of blowing out the gas uniformly into the bag main body, and filling the bag main body with gas in a securely mixed state. A gas sampling bag that is connected to a constant volume sampling passage, contains a pipe, on which a plurality of gas inlet/outlet holes are formed, in a bag main body, and allows the gas to flow into/out of the bag main body through the gas inlet/outlet holes. The opening of the plurality of gas inlet/outlet holes is formed in such a manner that the size is minimized while the pressure loss is suppressed so as not to increase as far as possible.

7 Claims, 4 Drawing Sheets

GAS SAMPLING BAG

BACKGROUND OF THE INVENTION

1. Field of the Invention

The present invention relates to a gas sampling bag and, more particularly, to a gas sampling bag that is connected to a constant volume sampling passage, contains a pipe, on which a plurality of gas inlet/outlet holes are formed, in a bag main body, and allows gas to flow into/out of the bag main body through the gas inlet/outlet holes.

2. Background Art

One of the sampling methods of emission gas exhausted from an automobile engine or the like is, for example, the constant volume sampling (CVS) method. In this CVS method, the emission gas having transiently changing flow rate is diluted with the air, and the flow rate of the diluted gas is defined as known flow rate, and the weight of components is calculated by using the diluted gas component concentration and the known flow rate.

In one of the measuring techniques of gas concentration of the CVS method, the sampled diluted gas is put in a gas sampling bag, and the gas in this gas sampling bag is supplied into a gas analyzer.

FIG. 5 schematically shows a conventional example of this gas sampling bag. In FIG. 5, reference numeral 51 denotes a gas sampling bag, and reference numeral 52 denotes a bag main body stretchably formed by gluing, for example, fluoroplastic sheets. Reference numeral 53 is a pipe made of, for example, fluoroplastic material of a circular cross-section provided inside the bag main body 52, and it is formed like a shape of 8 in plan view. In the middle of the pipe 53, a gas junction 54 is formed as a junction to an external gas passage, and a plurality of gas inlet/outlet holes 55 of proper small diameter are formed at uniform intervals on the periphery of the overall length of the pipe 53.

In the gas sampling bag 51 having such a configuration, the gas junction 54 is connected to the constant volume sampling passage through a valve and, by opening the valve, the gas from the constant volume sampling passage is introduced into the pipe 53 through the gas junction 54 and flows into the bag main body 52 through the plurality of gas inlet/outlet holes 55. In the bag main body 52, the gas is mixed securely, and a gas of uniform concentration is prepared. The gas sampling bag 51 is connected to a gas supply path to a gas analyzer through a valve and, by opening the valve, the gas in the bag main body 52 flows into the gas junction 54 through the plurality of gas inlet/outlet holes 55 and pipe 53 and flows out in the gas supply direction.

In the conventional gas sampling bag 51, however, in order to decrease the pressure loss of the gas when passing the gas inlet/outlet holes 55 as much as possible, when the inner diameter of the pipe 53 is, for example, 6 mm, this pipe 53 has 52 gas inlet/outlet holes 55 each having an opening diameter of, for example, 3 mm. In the gas sampling bag 51 formed in this manner, if the concentration changes significantly in the constant volume sampling passage, gas mixing in the bag main body 52 is not always sufficient, and the gas concentration in the bag main body 52 is not always uniform.

To avoid uneven gas concentration in the bag main body 52 of the gas sampling bag 51, the gas filling rate in the bag main body 52 may be raised, the gas injection time in the bag main body 52 may be extended, or the gas flowing rate into the bag main body 52 may be increased. However, in the gas sampling bag 51 connected to the constant volume sampling passage, the overall capacity of the bag main body 52 is limited, and cannot be increased simply in relation to the test mode duration and injection flow rate.

Under such restrictions, the present inventors investigated and discovered as follows: in the conventional gas sampling bag 51, it was attempted to minimize pressure loss of gas when passing the gas inlet/outlet holes, and all gas flowing into the pipe 53 through the gas junction 54 does not flow into the bag main body 52 through all of gas inlet/outlet holes 55, but flows into the bag main body 52 through a limited number of gas inlet/outlet holes 55 in the vicinity of the gas junction 54; therefore, there is a high possibility in that the gas was not mixed sufficiently.

SUMMARY OF THE INVENTION

It is therefore an object of the invention to present a gas sampling bag capable of blowing out the gas uniformly into the bag main body, and filling the bag main body with gas in a securely mixed state.

To achieve the object, the invention provides a gas sampling bag that is connected to a constant volume sampling passage, contains a pipe, on which a plurality of gas inlet/outlet holes are formed, in a bag main body, and allows the gas to flow into/out of the bag main body through the gas inlet/outlet holes, in which the opening of the plurality of gas inlet/outlet holes is formed in such a manner that the size is minimized while the pressure loss is suppressed so as not to increase as far as possible.

More specifically, it is comprehended that the opening size of the gas inlet/outlet holes is set so that the total area of the plurality of gas inlet/outlet holes formed in the pipe may be almost equal to or smaller than the opening sectional area of the pipe.

At the more detailed level, it is further comprehended that in the gas sampling bag having such a configuration, since the size of the opening of the plurality of gas inlet/outlet holes formed in the pipe contained in the bag main body is determined so that the pressure loss may be suppressed to be minimum so as not to increase as far as possible, the pressure in all the gas inlet/outlet holes is generally higher than in the conventional gas sampling bag; hence, the flow rate of the gas blown out from the gas inlet/outlet holes into the bag main body is higher. As a result, not limited to the plural gas inlet/outlet holes in the vicinity of the gas junction, the gas is blown out almost uniformly from all gas inlet/outlet holes opened in the pipe, and flows into the bag main body.

Therefore, in the gas sampling bag of the invention, the gas sampled in the bag main body is securely mixed and is contained; hence, a mixed gas of uniform concentration can be supplied as sample gas to the gas analyzer.

DETAILED DESCRIPTION OF THE PREFERRED EMBODIMENT

Figure 1:
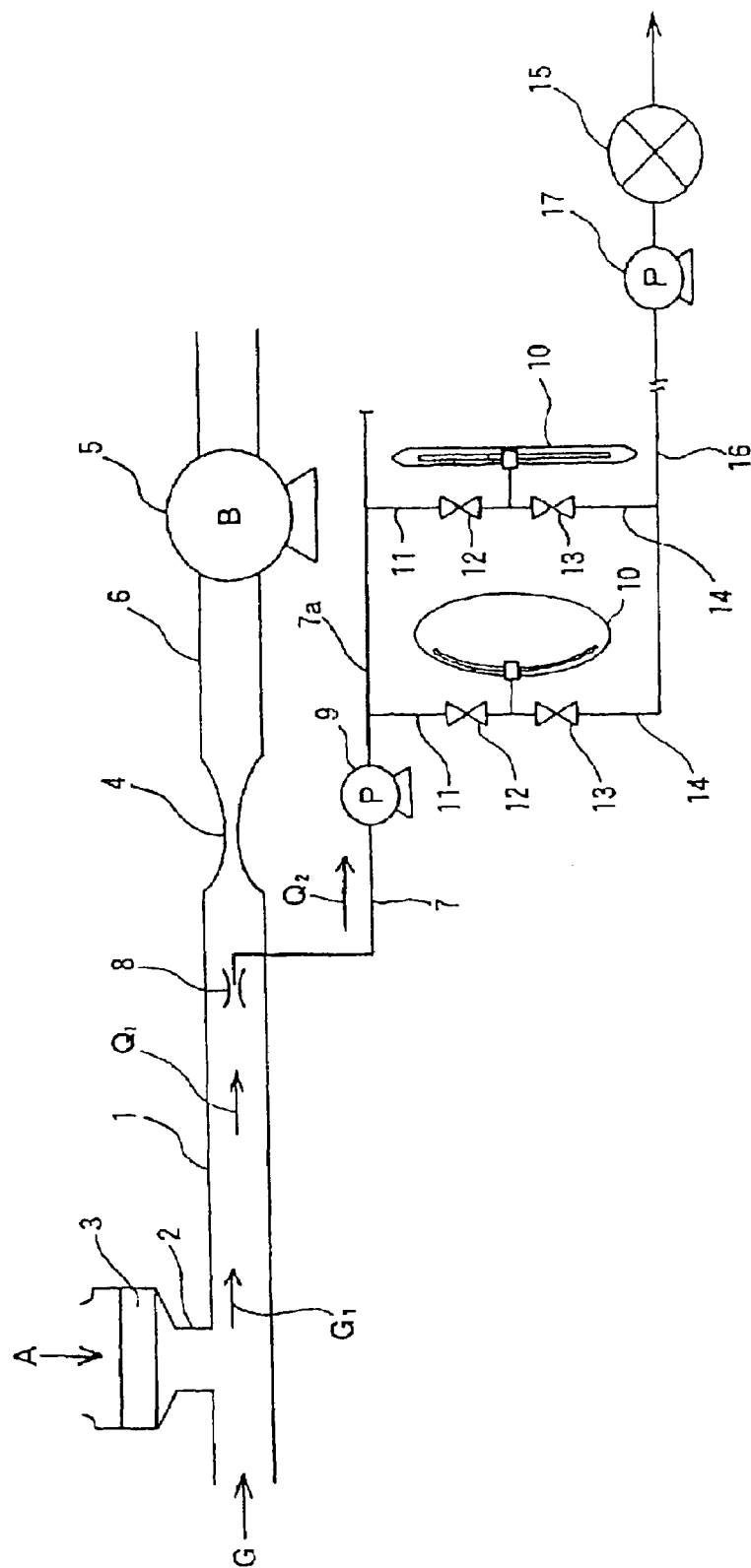
FIG. 1 is a diagram schematically showing an example of an automobile emission measuring apparatus in which a gas sampling bag of the invention is assembled.

FIGS. 1 to 4 show a preferred embodiment of the invention. FIG. 1 is a diagram schematically showing an example of an automobile emission measuring apparatus in which a gas sampling bag of the invention is assembled. In FIG. 1, reference numeral 1 denotes a sample gas diluting pipe, and emission gas G exhausted from an automobile engine as an emission source flows in from its upstream side. Reference numeral 2 denotes a diluting air introduction pipe connected to the sample gas diluting pipe 1, and diluting air A is introduced into the sample gas diluting pipe 1 through a filter 3. Reference numeral 4 denotes a venturi tube connected to the downstream side of the sample gas diluting pipe 1, and reference numeral 5 denotes a blower as a suction device provided in a duct 6 at the downstream side of this venturi tube 4, and emission gas diluted by the air A (hereinafter, referred to as "diluted emission gas") $G_1$ is sucked in at a specified flow rate $Q_1$ by the blower 5.

Reference numeral 7 is a constant volume sampling passage for sampling the diluted emission gas $G_1$ flowing through the sample gas diluting pipe 1 at a constant volume, and its highest upstream part has a gas sampling unit 8 composed of a venturi tube having the function similar to that of the venturi tube 4, while a suction pump 9 is provided at the downstream side, and a plurality of gas sampling bags (the structure thereof will be described later) 10 are provided in a downstream side passage 7a. That is, in the passage 7a, a plurality of branch passages 11 are connected, and a gas sampling bag 10 is connected to each branch passage 11 through an opening valve 12. Each gas sampling bag 10 is connected to a gas passage 14 having an opening valve 13, and the downstream side of these gas passages 14 is connected to a gas supply path 16 to a gas analyzer 15. Reference numeral 17 is a suction pump provided in the gas supply path 16.

In the constant volume sampling passage 7, supposing the flow rate when sucking the diluted emission gas $G_1$ by the gas sampling unit 8 to be $Q_2$, the suction pump 9 is operated so that $Q_2/Q_1$ may be always constant. More specifically, when filling one gas sampling bag 10 with the diluted emission gas $G_1$, the opening valve 13 provided in the gas passage 14 corresponding to this gas sampling bag 10 is closed, while the opening valve 12 provided in the branch passage 11 is opened, and the gas sampling bag 10 is filled with the diluted emission gas $G_1$ which is sampled in the constant ratio $Q_2/Q_1$. In the case of analyzing the diluted emission gas $G_1$ in the gas sampling bag 10, the opening valve 12 is closed and the opening valve 13 provided in the gas passage 14 is opened, so that the diluted emission gas $G_1$ is supplied as sample gas into the gas analyzer 15 through the gas supply path 16.

Figure 2:
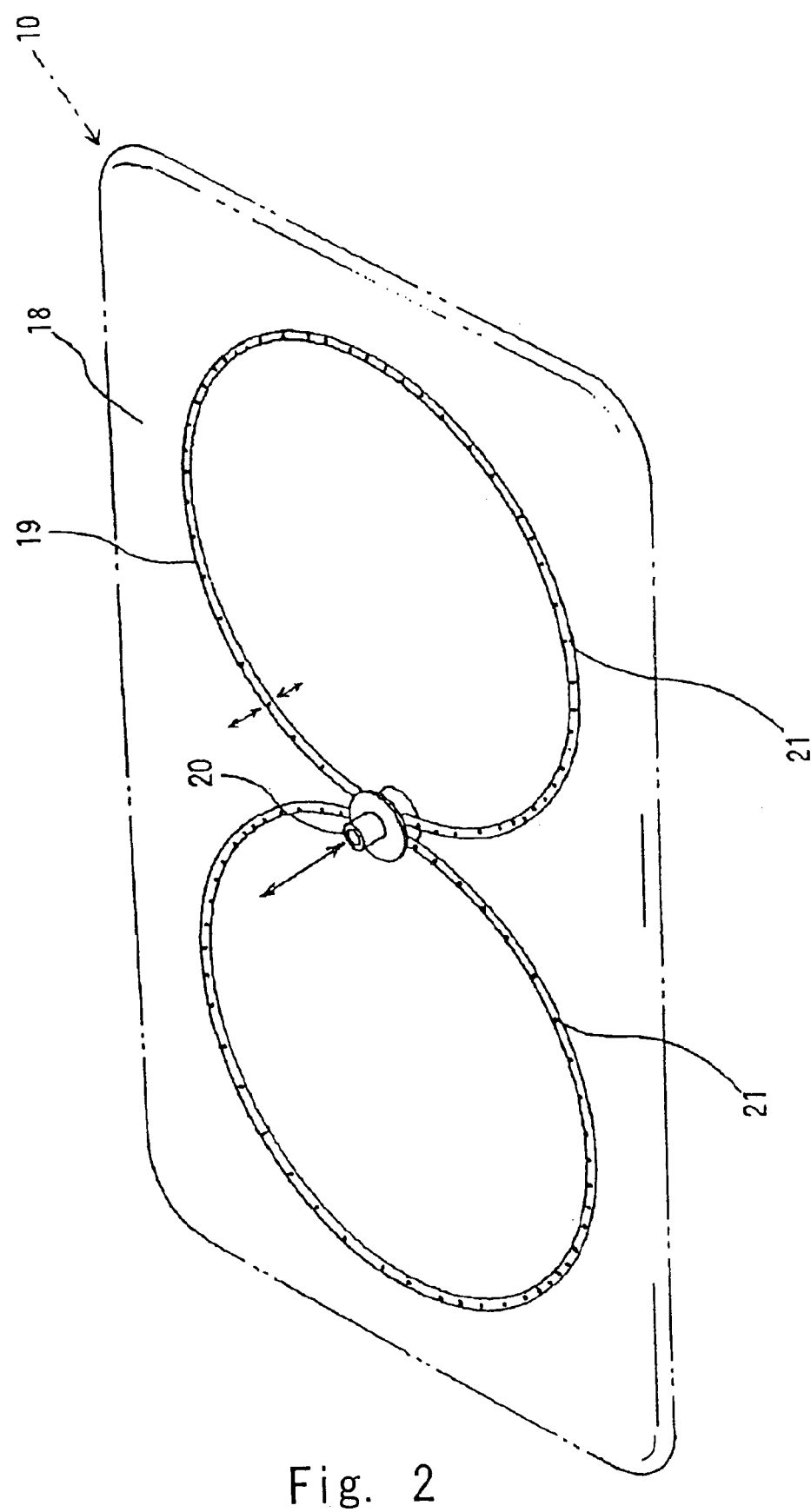
FIG. 2 is a diagram showing an example of the gas sampling bag.
Figure 3:
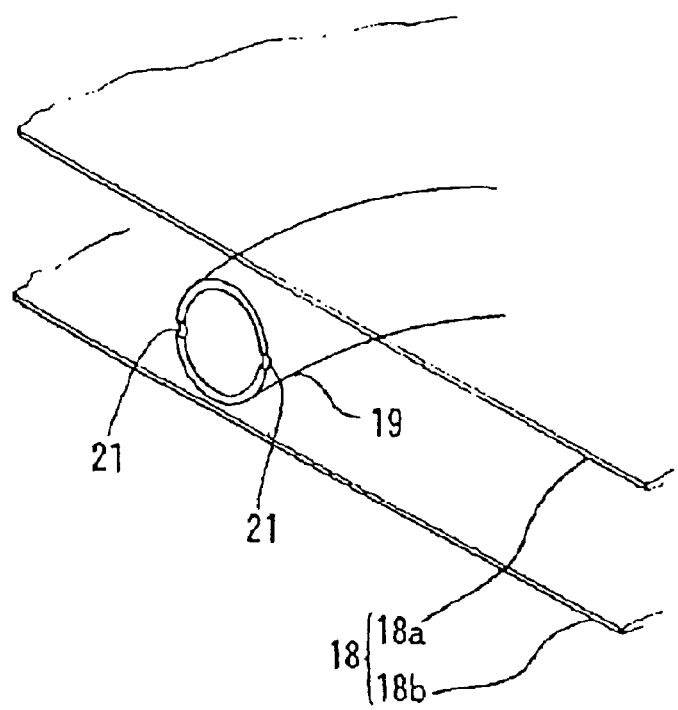
FIG. 3 is a partially enlarged view showing an open state of gas inlet/outlet holes in the gas sampling bag.

The gas sampling bag 10 is composed as shown in FIGS. 2 and 3, in which a bag main body 18 stretchably formed by gluing, for example, fluoroplastic sheets, and a pipe 19 made of, for example, fluoroplastic material of a circular cross-section is provided in its inside, for example, like a shape of 8 in plan view. In the middle of the pipe 19, a gas junction 20 is formed to be connected to the outside gas passages (in this example, passages 11, 14), and a plurality (52 in this example) of gas inlet/outlet holes 21 of proper small diameter are formed at uniform intervals on the periphery of the overall length of the pipe 19. The gas inlet/outlet holes 21 are opened so as not to be blocked by main body members 18a, 18g for forming the bag main body 18 as shown in FIG. 3, and more preferably are formed oppositely to the direction of diameter of the pipe 19.

The gas inlet/outlet holes 21 are opened so as to suppress and minimize the pressure loss so as not to increased as far as possible. More specifically, supposing the opening sectional area of the pipe 19 to be $S_{19}$ and the total opening area of the gas inlet/outlet holes 21 to be $S_{21}$, it is defined to satisfy the relation of $S_{19} \geqq S_{21}$, more preferably $S_{19} > S_{21}$.

More strictly, in order that the total opening area $S_{21}$ of the gas inlet/outlet holes 21 may be smaller than the opening sectional area $S_{19}$ of the pipe 19, the opening diameter of the gas inlet/outlet holes 21 is decreased, but the pressure loss due to reduction of diameter is set as small as possible, and extreme delay in injection and exhaust is avoided.

In the gas sampling bag 10 thus configured, since the size of the opening of the gas inlet/outlet holes 21 formed in the pipe 19 provided in the bag main body 18 is minimized so as to suppress the pressure loss so as not to increase as far as possible, the pressure in all of the gas inlet/outlet holes 21 is higher than in the conventional gas sampling bag; hence, the flow rate of the gas blown out from the gas inlet/outlet holes 21 into the bag main body 19 is increased. As a result, not limited to the plural gas inlet/outlet holes 21 in the vicinity of the gas junction 20, the gas is blown out almost uniformly from all gas inlet/outlet holes 21 opened in the pipe 19, and flows into the bag main body 18. Therefore, in the gas sampling bag 10, the gas is securely mixed and contained in the bag main body 18; hence, mixed gas of uniform concentration can be supplied as sample gas to the gas analyzer 15.

Figure 4:
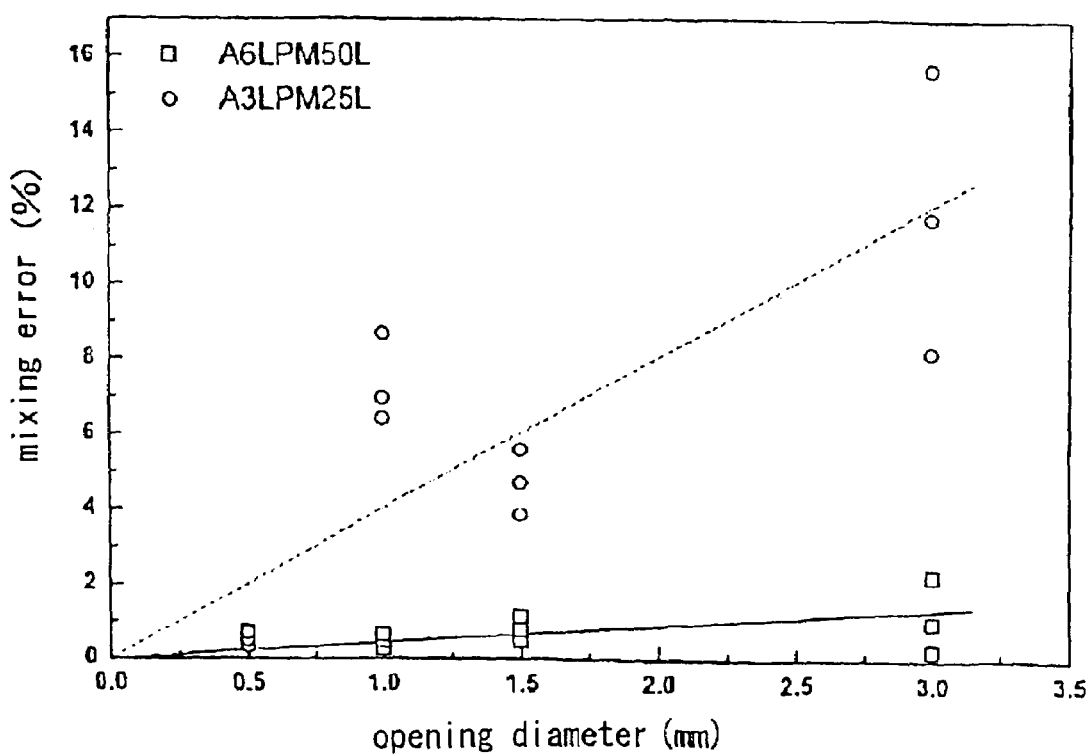
FIG. 4 is a diagram showing a relation between an opening diameter of gas inlet/outlet holes in the pipe and a mixing error.
Figure 5:
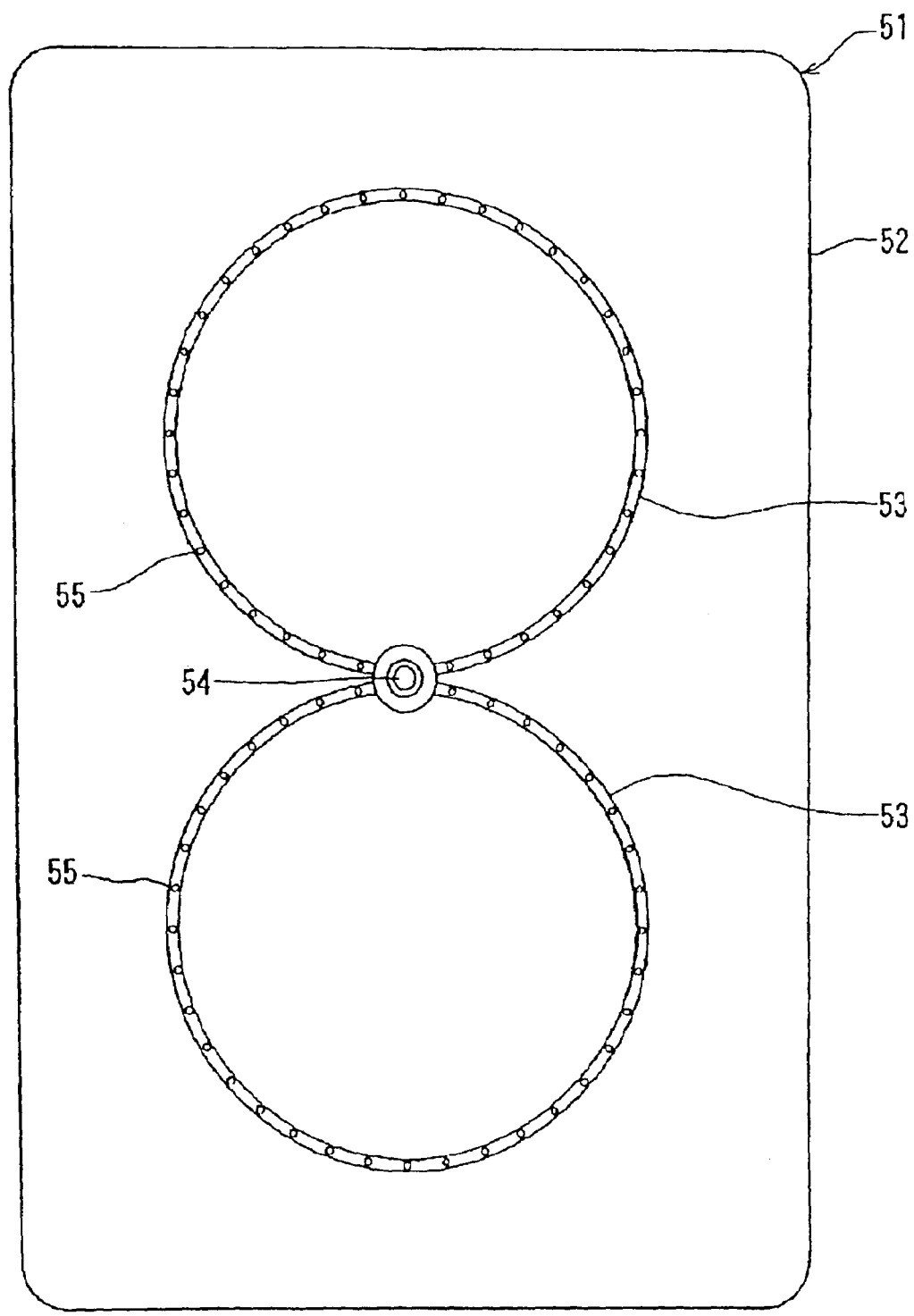
FIG. 5 is a diagram showing a conventional gas sampling bag.

FIG. 4 shows mixing errors (mixing effects) of gas in the gas sampling bag 10 when tested in the following conditions, by setting the opening diameter of the gas inlet/outlet holes 21 formed in the pipe 19 contained in the gas sampling bag 10 in three different sizes, 3 mm, 1.5 mm and 0.5 mm. In the figure, the square mark indicates the data when filling the gas sampling bag 10 at gas flow rate of 6 L/min, and the circle mark indicates the data at flow rate of 3 L/min. Both square and circle flow rates are overlapped at the hole diameter of 0.5 mm.

The outline (condition) of the test is as follows. In the test, in order to avoid adverse effects on the filling of gas sampling bag 10 with gas or mixing of gas in the bag, temperature difference and air stream were eliminated around the gas sampling bag 10. The opening diameter of the pipe 19 and the inside diameter of passages 11, 13 was commonly 6 mm. After filling the gas sampling bag 10 with $C_3H_8$ at 50 ppm at flow rate of 6 L/min and 3 L/min for 100 seconds, the gas sampling bag 10 was also filled with air for 400 seconds at the same flow rates (6 L/min and 3 L/min). After letting stand for 60 seconds, by applying impact to the gas sampling bag 10, mixing of the inside $C_3H_8$ and air was promoted, and the concentration of total hydrocarbon (THC) was measured after the gas sampling bag was shocked by patting and, on the basis of this reference value, the difference from the concentration before impact was calculated in the following formula, and the mixing error E (%) was determined.

$$E(\%) = [(\text{concentration after impact}) - (\text{concentration before impact})]/(\text{concentration after impact}) \times 100$$

As shown in FIG. 4, the mixing error is smaller in the hole diameter of 1.5 mm as compared with 3.0 mm of the gas inlet/outlet holes 21 opened in the pipe 19, and is further smaller in the hole diameter of 0.5 mm. That is, as the opening diameter of the gas inlet/outlet holes 21 becomes smaller, the mixing error is improved, and the error margin becomes smaller. In particular, when the opening diameter of the gas inlet/outlet holes 21 is 0.5 mm, at the flow rate of 6 L/min in the general sampling condition, the mixing error is reduced to 0.6%, that is, about ⅓ of the conventional one, and even at a small flow rate of 3 L/min, the mixing error is improved to 2%, that is, about ⅙ of the conventional one. The velocity of the gas passing through the gas inlet/outlet holes 21 can be increased to more than 30 times of the conventional one.

Thus, in the general sampling condition at flow rate of 6 L/min, preferably, the mixing error should be 1% or less, and as understood from FIG. 4, when the opening diameter of the gas inlet/outlet holes 21 is 1.0 mm or less, the mixing error of each case is 1% or less. Therefore, the opening diameter of gas inlet/outlet holes 21 is 1.0 mm or less, more preferably 0.5 mm.

As described above, by narrowing the diameter of gas inlet/outlet holes 21 formed in the pipe 19, the velocity of the gas passing the gas inlet/outlet holes 21 is increased, and the gas is sufficiently mixed and contained in the bag main body 18.

In the foregoing embodiment, when the opening diameter of the pipe 19 is 6 mm, the opening diameter of the gas inlet/outlet holes 21 is set at 0.5 mm, but not limited to this example, the opening diameter of the pipe 19 and the opening diameter of the gas inlet/outlet holes 21 may be set arbitrarily as far as the pressure loss is suppressed so as not to increase as far as possible. The number of gas inlet/outlet holes 21 formed in the pipe 19 is 52 in the shown example, but the same effects are obtained by forming a different number of holes.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A gas sampling bag for connecting to a constant volume sampling passage, the gas sampling bag comprising:
    a bag main body;
    a pipe, the pipe being located entirely within the bag main body and extending substantially about the length of the bag main body, the pipe having an opening defining an opening sectional area of the pipe, wherein a plurality of gas inlet/outlet holes are formed on the pipe to allow the gas to flow into/out of the bag main body through the gas inlet/outlet holes, and wherein the plurality of gas inlet/outlet holes are located substantially about the length of the bag main body; and
    a junction for connecting the opening of the pipe to the constant volume sampling passage, the pipe extending from the junction and extending substantially about the length of the bag main body,
    wherein the opening size of the gas inlet/outlet holes is set so that the total area of all gas inlet/outlet holes formed in the pipe is essentially not more than the opening sectional area of the pipe to blow out the gas generally uniformly from all gas inlet/outlet holes opened in the pipe and flow the gas into the bag main body while suppressing pressure loss along the pipe.

2. The gas sampling bag of claim 1 wherein the opening size of the gas inlet/outlet holes is set so that the total area of the plurality of gas inlet/outlet holes formed in the pipe is almost equal to the opening sectional area of the pipe.

3. The gas sampling bag of claim 1 wherein the opening size of the gas inlet/outlet holes is set so that the total area of the plurality of gas inlet/outlet holes formed in the pipe is less than the opening sectional area of the pipe.

4. The gas sampling bag of claim 1 wherein the bag main body is formed of fluoroplastic sheets.

5. The gas sampling bag of claim 1 wherein the plurality of inlet/outlet holes is composed of holes having generally the same size.

6. A gas sampling bag for connecting to a constant volume sampling passage, the gas sampling bag comprising:
    a bag main body;
    a pipe, the pipe being located within the bag main body and extending substantially about the length of the bag main body, the pipe having an opening defining an opening sectional area of the pipe, wherein a plurality of gas inlet/outlet holes are formed on the pipe to allow the gas to flow into/out of the bag main body through the gas inlet/outlet holes, and wherein the plurality of gas inlet/outlet holes are located substantially about the length of the bag main body;
    wherein the opening size of the gas inlet/outlet holes is set so that the total area of all gas inlet/outlet holes formed in the pipe is less than the opening sectional area of the pipe to blow out the gas generally uniformly from all gas inlet/outlet holes opened in the pipe and flow the gas into the bag main body while suppressing pressure loss along the pipe; and
    wherein the bag main body is formed of fluoroplastic sheets.

7. The gas sampling bag of claim 6 wherein the plurality of inlet/outlet holes is composed of holes having generally the same size.

* * * * *